United States Patent
Johns (10) Patent No.: US 10,667,520 B2
(45) Date of Patent: Jun. 2, 2020

(54) ACID COMPOSITIONS AND USES THEREOF

(71) Applicant: Chemtrade Solutions LLC, Parsippany, NJ (US)

(72) Inventor: Rex Johns, Jonesboro, AR (US)

(73) Assignee: Chemtrade Solutions, LLC, Parsippany, NJ (US)

( * ) Notice: Subject to any disclaimer, the term of this patent is extended or adjusted under 35 U.S.C. 154(b) by 0 days.

(21) Appl. No.: 15/855,068

(22) Filed: Dec. 27, 2017

(65) Prior Publication Data

US 2018/0184663 A1 Jul. 5, 2018

Related U.S. Application Data (60) Provisional application No. 62/440,082, filed on Dec. 29, 2016.

(51) Int. Cl.
| | |
|---|---|
| *A01N 59/12* | (2006.01) |
| *A01N 37/02* | (2006.01) |
| *A61L 9/01* | (2006.01) |
| *A01N 59/02* | (2006.01) |
| *A01N 59/06* | (2006.01) |
| *A61L 9/04* | (2006.01) |
| *A61L 9/14* | (2006.01) |
| *A01K 1/015* | (2006.01) |

(52) U.S. Cl.
CPC .............. *A01N 59/12* (2013.01); *A01N 37/02* (2013.01); *A01N 59/02* (2013.01); *A01N 59/06* (2013.01); *A61L 9/01* (2013.01); *A61L 9/044* (2013.01); *A61L 9/046* (2013.01); *A61L 9/14* (2013.01); *A01K 1/0152* (2013.01); *A61L 2209/21* (2013.01)

(58) Field of Classification Search
CPC ........ A01N 59/12; A01N 37/02; A01N 59/02; A01N 59/06; A61L 9/01; A61L 9/044; A61L 9/046; A61L 9/14
See application file for complete search history.

(56) References Cited

U.S. PATENT DOCUMENTS

| | | | |
|---|---|---|---|
| 5,192,610 A * | 3/1993 | Lorimer | C23C 8/34 428/336 |
| 9,301,440 B1 * | 4/2016 | Moore, Jr. | A01C 3/00 |
| 2012/0087965 A1 * | 4/2012 | Code | A01N 59/12 424/408 |

FOREIGN PATENT DOCUMENTS

| | | | |
|---|---|---|---|
| CN | 102312259 | * | 1/2012 |
| WO | 2016/130595 | | 8/2016 |

OTHER PUBLICATIONS

Dai et al., CN 102312259; published: Jan. 11, 2012; English Machine translation obtained on Mar. 18, 2019.*
Choi, Effect of Various Litter Amendments on Ammonia Volatilization and Nitrogen Content of Poultry Litter, J. Appl. Poult. Res., 2008, vol. 17, pp. 454-462.

* cited by examiner

*Primary Examiner* — Juliet C Switzer
*Assistant Examiner* — Genevieve S Alley
(74) *Attorney, Agent, or Firm* — Polsinelli PC (57) ABSTRACT

The present disclosure provides compositions and methods for using the compositions to treat animal facilities. In particular, the composition comprises a metal sulfate, an inorganic acid having a pKa of less than 1, and one or more organic acids.

16 Claims, 10 Drawing Sheets

ABSTRACT COMPOSITIONS AND USES THEREOF

CROSS REFERENCE TO RELATED APPLICATIONS

This application claims the benefit of U.S. Provisional Application No. 62/440,082, filed Dec. 29, 2016, the disclosure of which is hereby incorporated by reference in its entirety.

FIELD

The present disclosure relates to compositions and methods for using the compositions to treat animal facilities.

BACKGROUND

Litter amendments have been developed to manage ammonia level, acidity, and alkalinity and provide microbial control.

High ammonia levels in animal facilities can be detrimental to the health of both the animals and the farm workers. The ammonia gas results from the decomposition of animal wastes, and its formation is influenced by litter moisture, pH, and temperature. Thus, the main factors affecting the levels of ammonia in animal facilities are the litter conditions and the amount of ventilation. Litter amendments have been developed that acidify the litter and inhibit ammonia volatilization. For example, dry alum (e.g., aluminum sulfate) provides excellent ammonia control (i.e., acidifies the litter and suppresses ammonia volatilization), but has the drawback that it requires adequate litter moisture and time for activation. Other litter treatments contain sulfuric acid, which provides immediate acidification and ammonia control without an activation step, but the ammonia control is short lived.

High microbial levels in animal facilities can be detrimental to the health of the animals and can result in reduced weight gain and animal loss. Common microbial infections observed in animal facilities are caused by, for example, *Mycotoxicosis, Aspergillus* (e.g., Aspergillosis), *Bacillus, Camplybacter, Candidiasis, Clostridium* (e.g., *C. perfringens*), *Corynebacterium, Desulfovibrionales* (e.g., *Lawsonia*), *Enterococcus, Escherichia* (e.g., *E. coli*), *Histomonas meleagridis, Lactobacillus, Listeria, Pseudomonas, Salmonella, Staphylococcus*, and *Streptococcus*. Traditionally, a complete litter clean out was necessary to clean and disinfect the floor (i.e., pad), doorways, and curtain ledges, etc. to provide disease control. Then a litter amendment was applied to the pad to provide ammonia, pH, and microbial control.

What is needed, therefore, is a litter amendment that provides immediate and extended ammonia control without an extended activation period, and also provides antimicrobial properties to prevent common microbial infections.

SUMMARY

One aspect of present disclosure is the provision of a composition comprising a metal sulfate, an inorganic acid having a pKa of less than 1, and one or more organic acids.

A further aspect of the disclosure encompasses a method for inhibiting microbial growth of one or more microbes in an animal facility. The method comprises applying a composition to a surface of the animal facility to form a treated surface. The composition comprises a metal sulfate, an inorganic acid having a pKa of less than 1, and one or more organic acids.

Other aspects and iterations of the disclosure are described in more detail below.

DETAILED DESCRIPTION

Provided herein are compositions and methods for using the compositions. A composition comprises a metal sulfate, an inorganic acid having a pKa of less than 1, and one or more organic acids. Additional compositions comprise aluminum sulfate, sulfuric acid, and one or more organic acids. The compositions disclosed may also comprise iodine. The compositions disclosed herein have key properties; they provide ammonia control and inhibit the growth of microbes. In particular, the metal sulfate (e.g., aluminum sulfate) provides ammonia control and the organic acid(s) and iodine provide antimicrobial properties to the composition. In a preferred embodiment, the compositions described herein are in liquid form. Liquid compositions are faster acting than comparable dry compositions that need to adsorb moisture from the litter to activate. Thus, the liquid compositions have immediate onsets of activity.

Among the various uses for the liquid compositions include their use for reducing the pH of animal litter, reducing ammonia volatilization from animal litter, reducing moisture levels in animal litter, increasing the nitrogen content of animal litter for improved fertilizer value, reducing the runoff of soluble phosphorous from animal litters, reducing animal stress, and/or inhibiting microbial growth in animal facilities, thereby preventing microbial infections.

(I) Composition

One aspect of the present disclosure encompasses a composition comprising a metal sulfate, an inorganic acid having a pKa of less than 1, and one or more organic acids. An additional aspect of the present disclosure encompasses a composition comprising a metal sulfate, an inorganic acid having a pKa of less than 1, one or more organic acids, and iodine. Another aspect of the present disclosure encompasses a composition comprising aluminum sulfate, sulfuric acid, and one or more organic acids.

Each of the components and properties of the composition are detailed below.

(a) Components (i) Metal Sulfate

The compositions comprise a metal sulfate that serves to provide ammonia control. Upon contact with water, the metal sulfate in the composition undergoes hydrolysis to form buffered metal hydroxide intermediates and protons. Then, once contacted with an acid, the metal hydroxide intermediates are converted to an acidic metal sulfate, which is then hydrolyzed to form buffered metal hydroxide intermediates and additional protons. The protons can react with (or bind) volatile ammonia ($NH_3$) and form non-volatile ammonium ($NH_4^+$). Ammonium is a highly reactive ion that bonds with sulfates, nitrates, phosphates, or other anions to form ammonium salts. The presence of ammonium salts in animal litters improves their nutrient value use as fertilizers. Suitable metal sulfates include, without limit, aluminum sulfate, calcium sulfate, copper sulfate, iron(II) sulfate, magnesium sulfate, and combinations thereof. In some embodiments, the metal sulfate may be aluminum sulfate.

In general, the composition comprises a metal sulfate in an amount from about 15% to about 55% by weight of the total composition. In certain embodiments, the amount of metal sulfate present in the composition may be from about 20% to about 50% or from about 25% to about 45% by weight of the composition. In specific embodiments, the amount of metal sulfate present in the composition may be from about 30% to about 40% by weight of the composition. In some embodiments, the composition comprises a metal sulfate in an amount of about 30%, about 31%, about 32%, about 33%, about 34%, about 35%, about 36%, about 37%, about 38%, about 39%, or about 40% by weight of the composition.

(ii) Inorganic Acids

The compositions comprise an inorganic acid. The inorganic acid lowers the pH of the composition and provides protons to react with the metal sulfate. Suitable inorganic acids include those having a pKa of less than 1, less than 0, or less than −1 and include, without limit, benzenesulfonic acid, chloric acid, chromic acid, fluoroboric acid, fluorosulfuric acid, hexafluorophosphoric acid, hydrochloric acid, hydrobromic acid, hydroiodic acid, methanesulfonic acid, nitric acid, p-toluenesulfonic acid, perchloric acid, periodic acid, permanganic acid, sulfuric acid, trifluoromethanesulfonic acid, and combinations thereof. In some embodiments, the inorganic acid may be sulfuric acid.

The amount of inorganic acid included in the composition can and will vary depending, for example, on the other components of the composition and the desired functional properties of the composition. In some embodiments, the amount of inorganic acid present in the composition may be from about 1% to about 20%, from about 1% to about 15%, from about 1% to about 10%, from about 2% to about 10%, from about 2% to about 9%, from about 3% to about 9%, from about 4% to about 9%, or from about 5% to about 8% by weight of the composition. In specific embodiments, the amount of inorganic acid present in the composition may be from about 6% to about 8% by weight of the composition. In some embodiments, the composition comprises an inorganic acid in an amount of about 6%, about 7%, or about 8% by weight of the composition.

(iii) Organic Acids

The compositions comprise an organic acid or a combination of organic acids. The organic acid provides antimicrobial properties to the composition. The effectiveness of the organic acid as an antimicrobial agent depends on two factors: (1) hydrophobicity of the acid and (2) amount of undissociated acid in the composition. The more hydrophobic the acid, the more effective it is as an antimicrobial agent. Suitable organic acids include, without limit, acetic acid, adipic acid, benzoic acid, boric acid, butanoic acid, cinnamaldehyde, citric acid, formic acid, fumaric acid, glutaric acid, glycolic acid, lactic acid, mandelic acid, malic acid, maleic acid, malonic acid, propionic acid, sorbic acid, succinic acid, tartaric acid, and combinations thereof. In some embodiments, the organic acid may be propionic acid.

The amount of organic acid included in the composition can and will vary depending, for example, on the other components of the composition and the desired functional properties of the composition. In some embodiments, the amount of organic acid included in the composition may range from about 0.1% to about 10% by weight of the composition. In other embodiments, the amount of organic acid present in the composition may be from about 0.1% to about 8%, from about 0.1% to about 6%, from about 0.1% to about 4%, or from about 0.1% to about 2% by weight of the composition. In specific embodiments, the amount of organic acid present in the composition may be from about 0.5% to about 3% by weight of the composition. In some embodiments, the composition comprises an organic acid in an amount of about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% by weight of the composition.

(iv) Iodine

The composition may also comprise iodine or a source of iodine. The iodine provides antimicrobial properties to the composition. Further, it is believed that iodine kills bacterial and fungal spores. In some embodiments the iodine may include, without limit, iodine, iodide, iodine in a polymer complex, iodine in an ethanol-iodine complex, and combinations thereof. In some embodiments, the iodine may be nonylphenoxypoly (ethyleneoxy) ethanol-iodine complex. In other embodiments, the iodine may be polyoxyethylene-polyoxypropylene block polymer-iodine complex.

The amount of iodine included in the composition can and will vary depending, for example, on the other components of the composition and the desired functional properties of the composition. In some embodiments, the amount of iodine present in the composition may be from about 0.001% to about 0.03% or from about 0.003% to about 0.025% by weight of the composition. In specific embodiments, the amount of iodine present in the composition may be from about 0.005% to about 0.02% by weight of the composition. In some embodiments, the composition comprises iodine in an amount of about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, or about 0.02% by weight of the composition.

(v) Optional Additional Ingredients

The composition may also comprise optional additional ingredients. In some embodiments, the composition may include, without limit, adsorbers (e.g., clinoptilolite), pH adjusters (e.g., an acid, a base), surfactants (e.g., sodium dodecyl sulfate, diglyceride), wetting agents (e.g., di-alkyl sulfoccinate), solvents (e.g., water) and combinations thereof.

The amount of the additional ingredient(s) may be present in the composition from about 1% to about 30% by weight of the composition.

(vi) Exemplary Embodiments

In one embodiment, the composition comprises from about 30% to about 40% of aluminum sulfate, from about 0.5% to about 2% of propionic acid, and from about by 6% to about 8% sulfuric acid by weight of the composition.

In another embodiment, the composition comprises or consists of from about 30% to about 40% aluminum sulfate, from about 0.5% to about 2% propionic acid, from about by 6% to about 8% sulfuric acid, and from about 0.006% to about 0.018% iodine by weight of the composition.

(b) pH and Ammonia Binding Capacity

The pH of the composition disclosed herein can and will vary depending upon the identity of its components. In general, the composition has a pH of at least 1.0. In various embodiments, the composition may have a pH of about 1.0, about 1.25, about 1.5, about 1.75, about 2.0, about 2.25, about 2.5, about 2.75, or about 3.0.

The composition provides protons that lower the pH of the surface and/or the surrounding area to which the composition is applied. In some embodiments, the protons can react with (or bind to) ammonia, thereby forming ammonium. Thus, the composition has an ammonia binding capacity. In general, the ammonia binding capacity of the composition is at least 5 g of ammonia per 100 g of the liquid composition (i.e., at least 5%). In various embodiments, the ammonia binding capacity of the composition may be at least about 6 g, at least about 7 g, at least about 8 g, at least about 9 g, at least about 10 g ammonia, at least about 11 g ammonia, at least about 12 g, at least about 13 g, at least about 14 g, or at least about 15 g of ammonia per 100 g of the composition.

(II) Methods for Treating an Animal Facility

A further aspect of the present disclosure provides methods for using the compositions detailed above. Non-limiting examples of suitable uses include acidifying animal litters, acidifying the floors of animal facilities, reducing ammonia volatilization in animal facilities, improving air quality in animal facilities, reducing odor from animal facilities, reducing moisture levels in animal litters, reducing the levels of litter microorganisms, reducing the amount of energy needed to heat or ventilate animal facilities, increasing the nitrogen content of animal litters for improved fertilizer value, reducing the runoff of soluble phosphorous from animal litters, reducing animal stress, increasing animal weight gain, increasing animal productivity, improving feed conversion ratios, and improving the working environment of animal facility workers.

In general, the methods comprise applying the compositions to suitable surfaces to form treated surfaces. Suitable surfaces include, without limit, litter, floors (i.e., pads), doorways, curtain ledges, etc. of animal facilities. Animal litters comprise bedding material, animal wastes, and spilled feed. The floors of animal facilities are in contact or will be in contact with animal wastes (or the litter comprising animal wastes). It well known that the organic nitrogen in animal wastes (i.e., urea or uric acid) can be converted to ammonia by microorganisms. Formation of ammonia is favored under alkaline conditions (i.e., higher pH levels) and elevated temperatures.

In some embodiments, the method of use comprises treating an animal facility, wherein the method comprises applying the composition to a surface of the animal facility to form a treated animal facility. In other embodiments, the method of use comprises treating a surface in contact with or which will contact animal wastes, wherein the method comprises applying the composition to the surface to form a treated surface. In further embodiments, the method of use comprises treating an animal litter, wherein the method comprises applying the composition to the animal litter to form a treated animal litter.

Because the compositions comprise proton sources, application of the compositions lowers the pH of the surfaces to which the composition is applied. In general, application of the composition lowers the pH of the surface to a value of less than about 7.0. In some embodiments, the composition lowers the pH of the surface to a value of less than about 6.0, less than about 5.0, less than about 4.0, less than about 3.0, or less than about 2.0. Techniques for measuring pH are well known in the art. In general, the surface treated with the composition has a lower pH than a comparable untreated surface.

The acidification of the treated surfaces prevents volatilization of ammonia that may be formed from animal wastes present on or near the treated surfaces. That is, protons bind volatile ammonia ($NH_3$) and form non-volatile ammonium ($NH_4^+$). Ammonium is a highly reactive ion that bonds with sulfates, nitrates, phosphates, or other anions to form ammonium salts. The presence of ammonium salts in animal litters improves their nutrient value use as fertilizers. Thus, animal litters treated with the composition have higher levels of bound nitrogen than untreated litters. Accordingly, the treated litters have increased value as fertilizers as compared to untreated litters. Furthermore, animal litters treated with the composition have lower levels of soluble phosphorus than untreated litters. Thus, the treated animal litters have less soluble phosphorous runoff than untreated animal litters.

Inhibiting ammonia volatilization also reduces the levels of airborne ammonia in animal facilities. The generally recognized acceptable level of airborne ammonia in animal facilities is about 25 parts per million (ppm) or less. In some embodiments, the level of ammonia in the animal facility may be less than about 25 ppm, less than about 20 ppm, less than about 15 ppm, less than about 10 ppm, less than about 5 ppm, or less than about 1 ppm. Ammonia levels may be monitored and measured by a variety of means. Suitable means include ammonia meters, ammonia detection devices, ammonia sensors, ammonia gas monitors, colorimetric test strips, colorimetric paper, passive colorimetric tube detectors for ammonia, active colorimetric tubes for ammonia, and other detection means well-known in the art. In general, animal facilities treated with the composition have lower levels of airborne ammonia than comparable untreated animal facilities.

Reducing airborne ammonia levels in animal facilities, therefore, improves air quality in animal facilities. Improved air quality (i.e., low ammonia levels) improves the quality of life for animals housed in the animal facility and reduces the physiological stress of the animals. Animals with reduced stress generally have increased weight gain, better feed conversion ratios, increased productivity (e.g., increased egg production, increased milk production, etc.) and/or fewer infections or diseases than stressed animals. Improved air quality (i.e., low ammonia levels) also provides better working conditions for the animal facility workers. Reducing the levels of airborne ammonia may also reduce the amount of energy needed to ventilate and/or heat the animal facilities. Lastly, inhibiting ammonia volatilization may also reduce odor from animal litter and/or animal facilities.

In some embodiments, the compositions may be used to provide microbial control of an animal facility. One aspect of the composition reduces the pH of the treated surfaces which creates an unfavorable environment for the propagation of microorganisms that contribute to ammonia control.

Thus, less ammonia may be formed on or near surfaces treated with the compositions. Additionally, the acidification of the treated surface may create conditions unfavorable for the proliferation of undesirable microorganisms that can infect or cause diseases in the animals housed in the animal facility. As noted elsewhere, the compositions may include iodine. As known to one of ordinary skill in the art, iodine provides antimicrobial properties. In some embodiments, the composition reduces the number of microorganisms by about 10%, about 20%, about 30%, about 40%, about 50%, about 60%, about 70%, about 80%, about 90%, about 100%, or more than 100% relative to a surface that was not treated with the composition.

In specific embodiments, the microbe may be a gram positive bacterium such as, for example, *Clostridium* (e.g., *C. perfringens*), *Bacillus, Lactobacillus, Listeria, Corynebacterium, Enterococcus, Staphylococcus, Streptococcus*, and so forth. In other embodiments, the microbe may be a gram negative bacterium such as, for example, *Escherichia* (e.g., *E. coli*), *Salmonella, Camplybacter, Pseudomonas, Desulfovibrionales* (e.g., *Lawsonia*), and so forth. In additional embodiments, the microbe may be a protozoan such as, for example, *Histomonas meleagridis*, and so forth.

As detailed elsewhere, the compositions comprise immediate and delayed sources of protons. Accordingly, the compositions disclosed herein generally have a rapid onset of activity as well as a prolonged or extended duration of activity. Protons are immediately provided by the acids included in the compositions. As noted elsewhere, the preferred form of the composition is liquid. Thus, the liquid compositions disclosed herein do not require moisture from the litter for activation.

The onset of activity and the duration of activity of the liquid compositions can and will vary depending, for example, on the application rate, ventilation rate, ambient temperature, depth of litter layer, and so forth. In some embodiments, the liquid compositions may reduce pH and/or reduce ammonia levels within about 1 hour, within about 6 hours, within 12 hours, or within 24 hours of application. In other embodiments, the liquid compositions may reduce pH and/or control ammonia to levels of 25 ppm or less for at least about 7 days, at least about 9 days, at least about 11 days, at least about 13 days, at least about 15 days, at least about 17 days, at least about 19 days, at least about 21 days, or longer than about 21 days.

The amount of the liquid composition applied to an animal litter layer or floor of an animal facility can and will vary depending, for example, upon the temperature and amount of ventilation in the animal facility, the age and/or moisture content of the litter layer, and so forth. In various embodiments, the liquid composition may be applied at a rate from about 0.5 to about 4.5 gallons per 100 $ft^2$, from about 1 to about 4 gallons per 100 $ft^2$, from about 1.5 to about 3.5 gallons per 100 $ft^2$, or from about 2 to about 3 gallons per 100 $ft^2$ of surface area. The liquid composition may be applied to the surface using a spot sprayer, spray truck, boom spray truck, or any other sprayer known in the field.

In some embodiments, the liquid composition may be applied to an animal litter surface or animal facility floor surface without a preheating step. Ammonia production is promoted by high temperatures and high pH (i.e., alkaline conditions). Thus, temporarily increasing the temperature of the animal facility prior to animal placement may promote ammonia generation and volatilization from the litter layer during the "burn off" period. Because the liquid compositions disclosed herein have immediate activity, a burn off period is not required prior to application of the liquid composition. In other embodiments, the liquid composition may be applied to an animal litter surface or animal facility floor surface after a preheating step. In general, however, the liquid composition is typically applied to the desired surface up to several days prior to animal placement to ensure that the levels of ammonia in the enclosure are 25 ppm or less at the time of animal placement.

The compositions disclosed herein may be used in a variety of animal facilities. In some embodiments, the animal facility may house livestock animals such as poultry (e.g., boilers, turkeys, ducks, geese, pheasants, game birds, layers, etc.), cattle (e.g., dairy, beef, veal, etc.), pigs, sheep, and goats. In other embodiments, the animal facility may be used by companion animals such as cats, dogs, horses, rodents (e.g., mice, rats, hamsters, gerbils, guinea pigs), and the like. In other embodiments, the animal facility may be used by zoo animals such as monkeys, chimpanzees, lions, tigers, elephants, giraffes, and so forth. In certain embodiments, the animal facility may be a poultry facility. In specific embodiments, the animal facility may be a chicken facility.

Definitions

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

The term "alum" refers to aluminum sulfate.

The term "ammonia control," as used herein, refers to means for maintaining atmospheric ammonia levels at 25 ppm or less by the inhibition of ammonia volatilization.

An "immediate source of protons" refers to a compound (i.e. a Brnsted-Lowry acid) that readily can donate a proton to a base.

As used herein, a "delayed source of protons" refers to a compound that can generate protons during its hydrolysis. Additionally, the compound (i.e., a Lewis acid) can accept an electron pair.

The term "animal litter," as used herein, refers to a mixture of animal excreta, spilled feed, and bedding material.

The term "poultry litter," as used herein, refers to a mixture of poultry excreta, spilled feed, feathers, and material used as bedding in poultry operations. Common bedding materials include wood shavings, sawdust, peanut hulls, shredded sugar cane, straw, and other dry, absorbent, low-cost organic materials. The bedding materials help absorb moisture, thereby limiting the production of ammonia and harmful pathogens.

The term "inhibiting," as used herein, refers to reducing or preventing further growth of one or more microbes or preventing one or more microbes from growing on a surface of an animal facility.

Acronyms used herein include "cfu" for "colony forming units," "MPN" for "most probable number," and "TPC" for "total plate count."

As various changes could be made in the above-described animals, cells and methods without departing from the scope of the invention, it is intended that all matter contained in the above description and in the examples given below, shall be interpreted as illustrative and not in a limiting sense.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Preparation of Compositions

Composition A was prepared by mixing 1.6 gallons of solution 1 (comprising 25-50% propionic acid and 0.42% of iodine as polyoxyethylene-polyoxypropylene block polymer-iodine complex), 0.4 gallons of solution 2 (comprising 1.75% of iodine as nonylphenoxypoly (ethyleneoxy) ethanol-iodine complex), and 100 gallons of solution 3 (comprising 35-37% aluminum sulfate and 7% sulfuric acid). The mixture was mixed until a homogenous mixture was obtained. The final product (composition A) contains about 35% aluminum sulfate, about 7% sulfuric acid, about 0.3-0.8% propionic acid, and about 0.014% iodine by weight of the composition.

Composition B was prepared by mixing 1.2 gallons of solution 4 (comprising 70.5% propionic acid), 0.4 gallons of solution 2 (comprising 1.75% of iodine as nonylphenoxypoly (ethyleneoxy) ethanol-iodine complex), and 100 gallons of solution 3 (comprising 35-37% aluminum sulfate and 7% sulfuric acid). The mixture was mixed until a homogenous mixture was obtained. The final product (composition B) contains about 35% aluminum sulfate, about 7% sulfuric acid, about 0.9% propionic acid, and about 0.007% iodine by weight of the composition.

Example 2. Disease Control—Field Tests

A field test was conducted to compare disease prevention of the liquid compositions described in Example 1, above, to that of the component solutions under normal broiler house conditions. Four isolated broiler houses were used to test each composition, individually and combinations thereof. Solution 3 (325 gallons), solutions 2 and 3 (325 gallons of solution 3 and 3.25 gallons of solution 2), solutions 1 and 3 (325 gallons of solution 3 and 2.5 gallons of solution 1), and composition A (325 gallons of solution 3, 1.3 gallons of solution 2, and 5.2 gallons of solution 1) were applied at a rate of 25 gallons per 1,000 ft². Minimum ventilation at placement may be 28 sec. [on]: 280 sec. [off]. The test house ventilation may be increased to 30 sec. [on]: 270 sec. [off] on the second day after placement (because the ammonia levels exceeded 25 ppm). The litter amendments were applied three days prior to bird placement.

Drag swabs were taken pre-treatment, 24 hours post-treatment, day of placement, and at 3 and 45 days after placement to determine the identity and counts of various microbes present in the waterline.

Tables 1-3 present the levels of Salmonella (Table 1), E. coli (Table 2), and Clostridium (Table 3) obtained after bird placement.

TABLE 1

Field Trial - Disease Control (Salmonella) (MPN/swab)

| Broiler House | Composition | | | |
| --- | --- | --- | --- | --- |
| | Solution 3<br>1 | Solutions<br>2 & 3<br>2 | Solutions<br>1 & 3<br>3 | A<br>4 |
| Pre-treatment | <4 | <4 | <4 | <4 |
| Post-treatment | <4 | <4 | <4 | <4 |
| Day of placement | <4 | <4 | <4 | <4 |
| Day 3 | <4 | <4 | 230267 | 70 |
| Day 45 | <4 | <4 | <4 | <4 |

TABLE 2

Field Trial - Disease Control (E. coli) (cfu/swab)

| Broiler House | Composition | | | |
| --- | --- | --- | --- | --- |
| | Solution 3<br>1 | Solutions<br>2 & 3<br>2 | Solutions<br>1 & 3<br>3 | A<br>4 |
| Pre-treatment | <10 | <10 | <10 | <10 |
| Post-treatment | 340 | 10 | <10 | <10 |
| Day of placement | 820 | <10 | 10 | <10 |
| Day 3 | 17000 | 39000 | 2600000 | 130000 |
| Day 45 | 1100 | 4200 | 150 | 1000 |

TABLE 3

Field Trial - Disease Control (Clostridium) (spores/swab)

| Broiler House | Composition | | | |
| --- | --- | --- | --- | --- |
| | Solution 3<br>1 | Solutions<br>2 & 3<br>2 | Solutions<br>1 & 3<br>3 | A<br>4 |
| Pre-treatment | 120 | 100 | 170 | 50 |
| Post-treatment | 5500 | 2050 | <10 | <10 |
| Day of placement | 900 | 1010 | 2800 | 1100 |
| Day 3 | 5000 | 300 | 4000 | 3000 |
| Day 45 | <10 | <10 | <10 | <10 |

Example 4. Disease Control—Field Tests

A field test was conducted to compare disease prevention of the liquid compositions described in Example 1, above, to that of the component solutions under normal broiler house conditions. A total of 24 isolated broiler houses were used to test the solutions and combinations thereof as described in Example 1. Solution 3 (325 gallons), solutions 2 and 3 (325 gallons of solution 3 and 3.25 gallons of solution 2), solutions 1 and 3 (325 gallons of solution 3 and 2.5 gallons of solution 1), and composition A (325 gallons of solution 3, 1.3 gallons of solution 2, and 5.2 gallons of solution 1) were applied at a rate of 25 gallons per 1,000 ft². Minimum ventilation at placement may be 28 sec. [on]: 280 sec. [off]. The test house ventilation may be increased to 30 sec. [on]: 270 sec. [off] on the second day after placement (because the ammonia levels exceeded 25 ppm). The litter amendments were applied three days prior to bird placement.

Drag swabs were taken pre-treatment, 24 hours post-treatment, day of placement, and at various time points (as indicated) after placement to determine the identity and counts of various microbes present on the floor or pad of the broiler house.

Figure 1A:
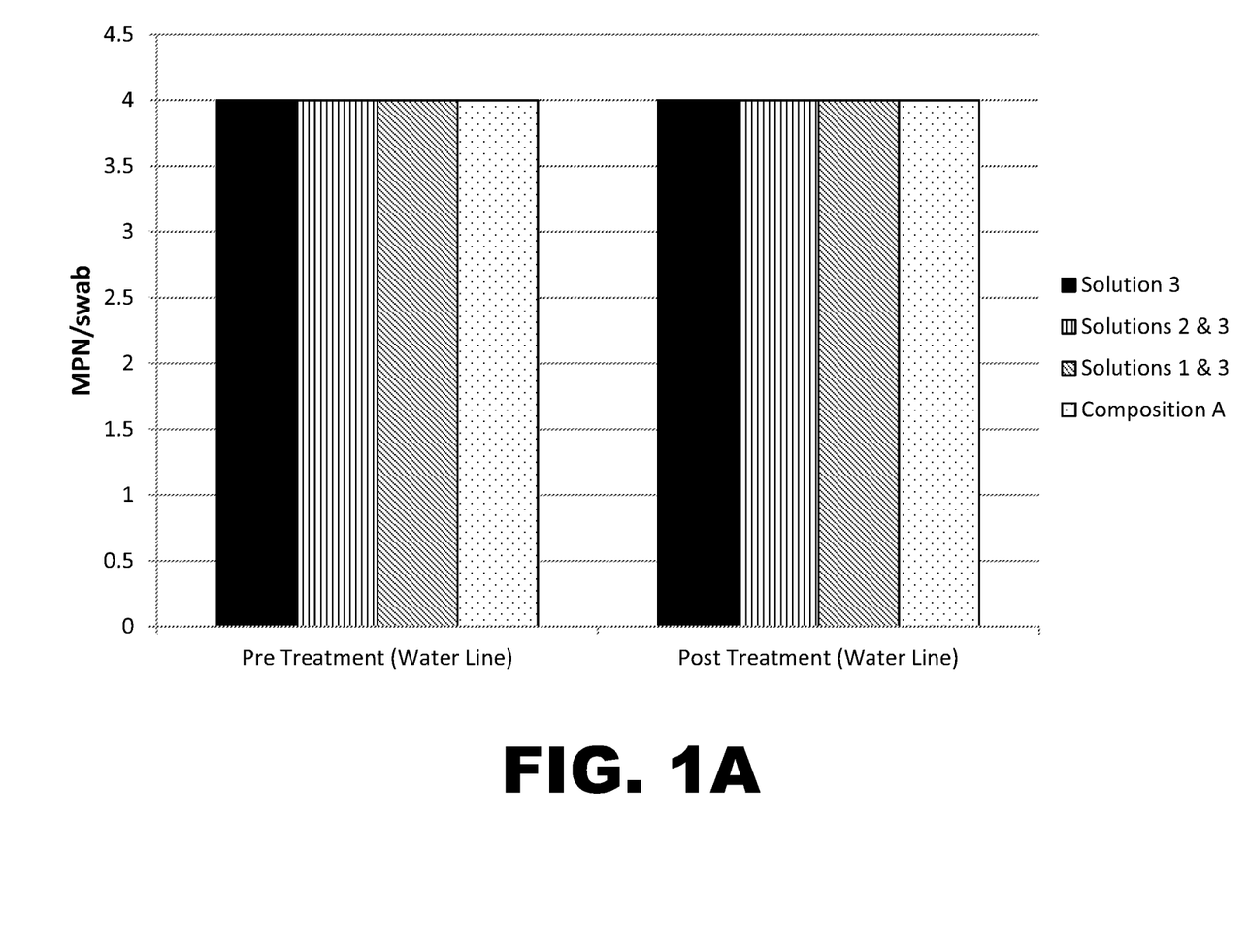
FIG. 1A, FIG. 1B, FIG. 1C, FIG. 1D, FIG. 1E, and FIG. 1F depict graphs showing amount of *Salmonella* (FIG. 1A), *Clostridium* (FIG. 1B), and *E. coli* (FIG. 1C) obtained from swabs collected from the water lines of boiler houses treated with solution 3, solutions 2 and 3, solutions 1 and 3, and composition A and graphs showing amount of *Salmonella* (FIG. 1D), *Clostridium* (FIG. 1E), and *E. Coli* (FIG. 1F) obtained from swabs collected from the feed lines of boiler houses treated with solution 3, solutions 2 and 3, solutions 1 and 3, and composition A.
Figure 1B:
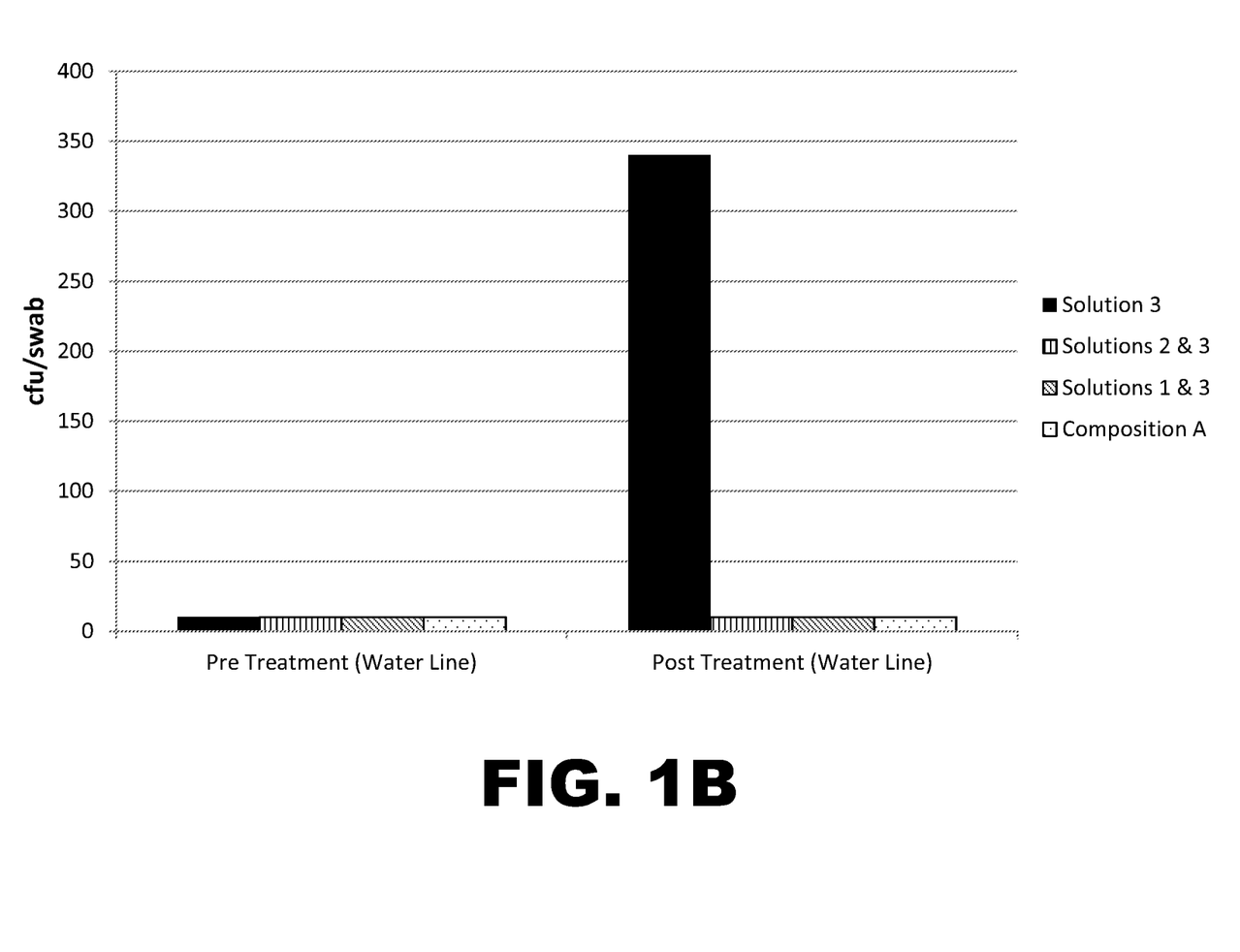
Figure 1C:
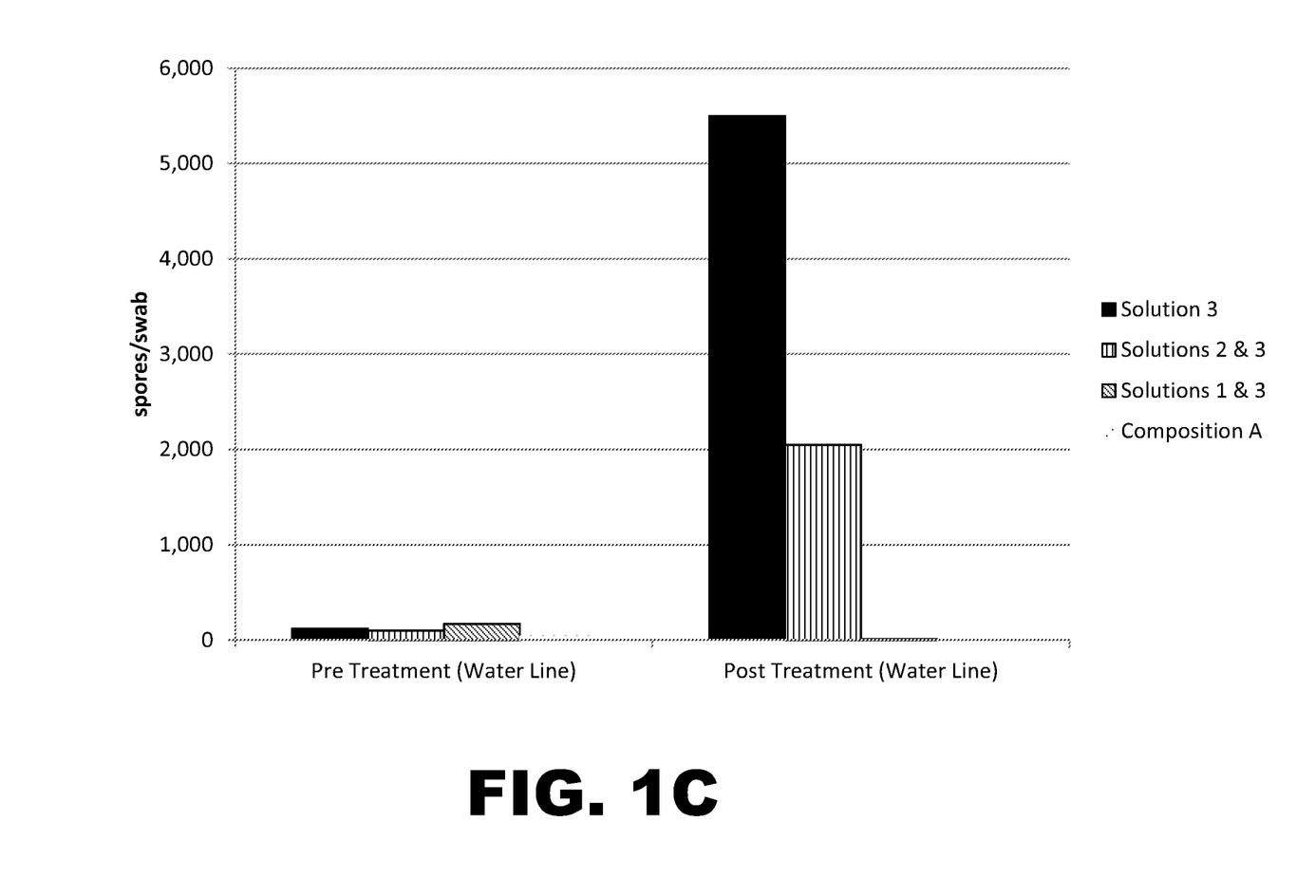

Tables 4-6 present the levels of *Salmonella* (Table 4 and FIG. 1A), *E. coli* (Table 5 and FIG. 1B), and *Clostridium* (Table 6 and FIG. 1C) obtained at the water line after bird placement.

TABLE 4

Field Trial - Disease Control (*Salmonella*) (MPN/swab) - Farm 1

| House Condition | Solutions/Composition | | | | |
|---|---|---|---|---|---|
| | 1 <br> 3 | 2 <br> 2 & 3 | 3 <br> 1 & 3 | 4 <br> A | Average |
| Pre-treatment | 4 | 4 | 4 | 4 | 4 |
| Post-treatment (24 hours) | 4 | 4 | 4 | 4 | 4 |
| Day of placement | 4 | 4 | 4 | 4 | 4 |
| Day 3 | 4 | 4 | 230267 | 70 | 57586 |

TABLE 5

Field Trial - Disease Control (*E. coli.*) (cfu/swab) - Farm 1

| House Condition | Solutions/Composition | | | | |
|---|---|---|---|---|---|
| | 1 <br> 3 | 2 <br> 2 & 3 | 3 <br> 1 & 3 | 4 <br> A | Average |
| Pre-treatment | 10 | 10 | 10 | 10 | 10 |
| Post-treatment (24 hours) | 340 | 10 | 10 | 10 | 93 |
| Day of placement | 820 | 10 | 10 | 10 | 213 |
| Day 3 | 17000 | 39000 | 2600000 | 130000 | 696500 |

TABLE 6

Field Trial - Disease Control (*Clostridium*) (spores/swab) - Farm 1

| House Condition | Solutions/Composition | | | | |
|---|---|---|---|---|---|
| | 1 <br> 3 | 2 <br> 2 & 3 | 3 <br> 1 & 3 | 4 <br> A | Average |
| Pre-treatment | 120 | 100 | 170 | 50 | 110 |
| Post-treatment (24 hours) | 5500 | 2050 | 10 | 10 | 1893 |
| Day of placement | 900 | 1010 | 2800 | 1100 | 1453 |
| Day 3 | 5000 | 300 | 4000 | 3000 | 3075 |

Figure 1D:
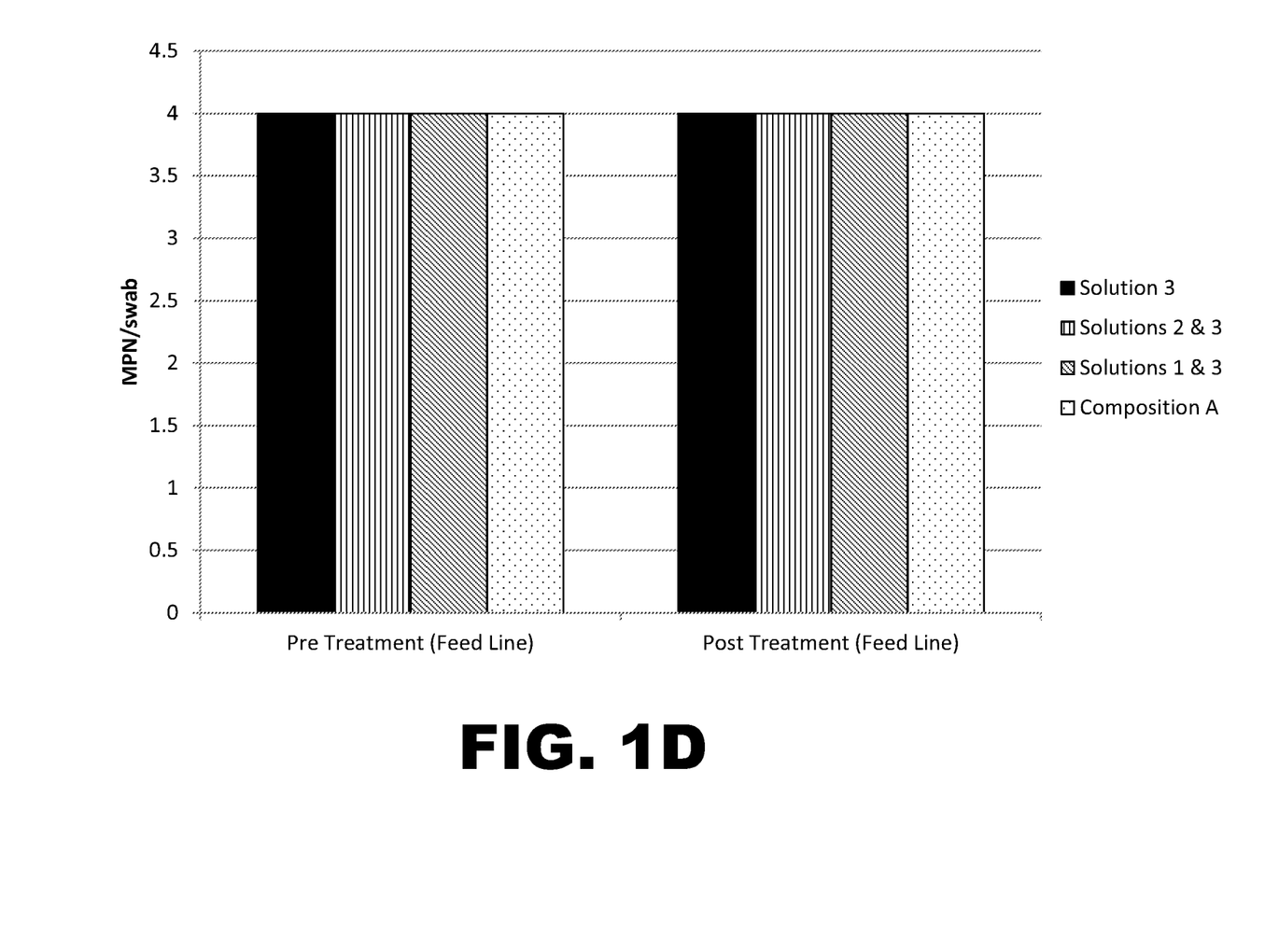
Figure 1E:
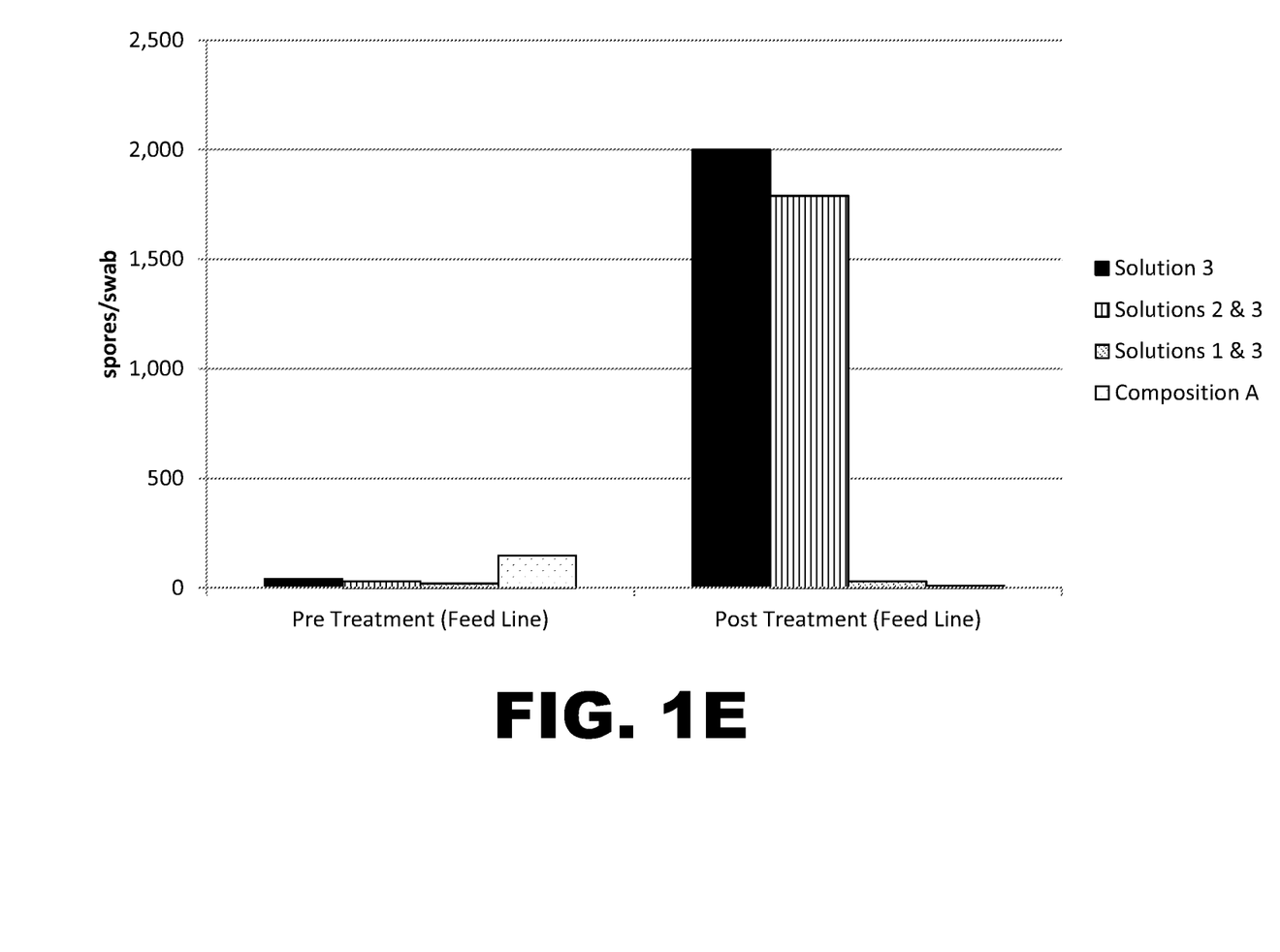
Figure 1F:
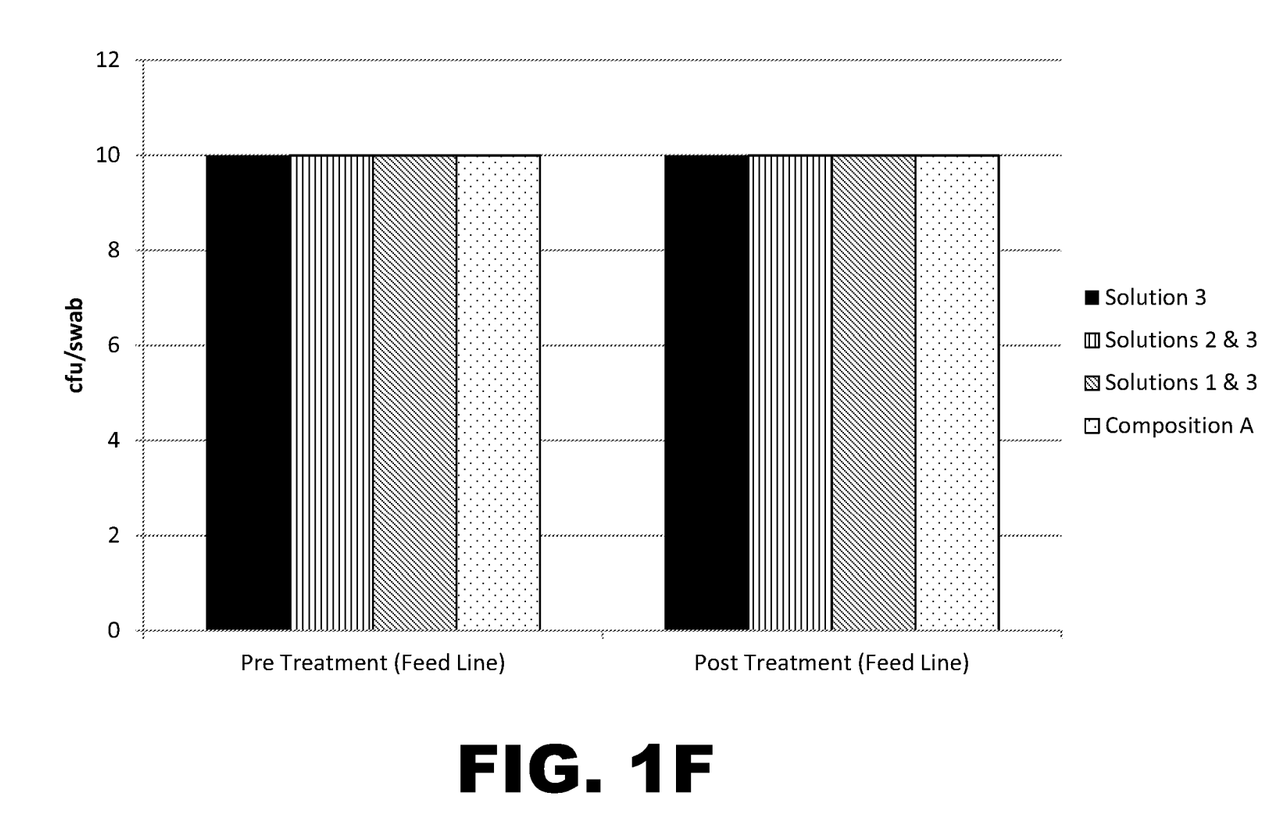

Tables 7-9 present the levels of *Salmonella* (Table 5 and FIG. 1D), *E. coli* (Table 6 and FIG. 1E), and *Clostridium* (Table 7 and FIG. 1F) obtained at the feed line after bird placement.

TABLE 7

Field Trial - Disease Control (*Salmonella*) (MPN/swab) - Farm 2

| House Condition | Solutions/Composition | | | | |
|---|---|---|---|---|---|
| | 1 <br> 3 | 2 <br> 2 & 3 | 3 <br> 1 & 3 | 4 <br> A | Average |
| Pre-treatment | 4 | 4 | 4 | 4 | 4 |
| Post-treatment (24 hours) | 4 | 4 | 4 | 4 | 4 |
| Day of placement | 4 | 4 | 4 | 4 | 4 |
| Day 3 | 4 | 4 | 230267 | 123 | 57600 |

TABLE 8

Field Trial - Disease Control (*E. coli.*) (cfu/swab)- Farm 2

| House Condition | Solutions/Composition | | | | |
|---|---|---|---|---|---|
| | 1 <br> 3 | 2 <br> 2 & 3 | 3 <br> 1 & 3 | 4 <br> A | Average |
| Pre-treatment | 10 | 10 | 10 | 10 | 10 |
| Post-treatment (24 hours) | 10 | 10 | 10 | 10 | 10 |
| Day of placement | 2100 | 10 | 10 | 10 | 533 |
| Day 3 | 55000 | 210000 | 2000 | 7000 | 60625 |

TABLE 9

Field Trial - Disease Control (*Clostridium*) (spores/swab) - Farm 2

| House Condition | Solutions/Composition | | | | |
|---|---|---|---|---|---|
| | 1 <br> 3 | 2 <br> 2 & 3 | 3 <br> 1 & 3 | 4 <br> A | Average |
| Pre-treatment | 40 | 30 | 20 | 148 | 60 |
| Post-treatment (24 hours) | 2000 | 1790 | 30 | 10 | 958 |
| Day of placement | 1700 | 940 | 1400 | 420 | 1115 |
| Day 3 | 19100 | 1500 | 180 | 2000 | 5695 |

Tables 10 and 11 present the levels of *E. coli* (Table 10) and *Clostridium* (Table 11) obtained at the litter surface between the water and feeder lines after bird placement.

TABLE 10

Field Trial - Disease Control (*E. coli.*) (cfu/swab) - Farm 3 (Full house)

| House Condition | Solutions/Composition | | | | |
|---|---|---|---|---|---|
| | 1 | 2 | 3 <br> 1 & 3 | 4 | Average |
| Pre-treatment | 3000 | 1100 | 13000 | 22000 | 9775 |
| Day 13 | | 51000 | 38000 | 33000 | 40667 |
| Day 16 | 44000 | 26000 | 64000 | 30000 | 41000 |
| Day 19 | 77000 | 70000 | 130000 | 62000 | 84750 |
| Day 22 | 66000 | 230000 | 87000 | 160000 | 135750 |

TABLE 11

Field Trial - Disease Control (*Clostridium*) (spores/swab) - Farm 3 (Full house)

| House Condition | Solutions/Composition | | | | |
|---|---|---|---|---|---|
| | 1 | 2 | 3 <br> 1 & 3 | 4 | Average |
| Pre-treatment | 1100 | 800 | 2000 | 300 | 1050 |
| Day 13 | | <10 | 1400 | 500 | 950 |
| Day 16 | 600 | 700 | 1100 | 400 | 700 |
| Day 19 | 500 | 1300 | 500 | 800 | 775 |
| Day 22 | 1600 | 2100 | 1300 | 1800 | 170 |

Tables 12 and 13 present the levels of *E. coli* (Table 12) and *Clostridium* (Table 13) obtained at the litter surface down the water lines after bird placement.

TABLE 12

Field Trial - Disease Control (*E. coli.*) (cfu/swab) - Farm 4 (Half house)

| House Condition | Solutions/Composition | | | | Average |
|---|---|---|---|---|---|
| | 1 | 2 | 3 | 4 | |
| | | 1 & 3 | | | |
| Pre-treatment | 26000 | 6700 | 17000 | 1900 | 12900 |
| Day 13 | 47000 | 5200 | 86000 | 120000 | 64550 |
| Day 16 | 63000 | 52000 | 80000 | 120000 | 78750 |
| Day 19 | 270000 | 260000 | 110000 | 200000 | 210000 |
| Day 22 | 190000 | 180000 | 220000 | 210000 | 200000 |

TABLE 13

Field Trial - Disease Control (*Clostridium*) (spores/swab) - Farm 4 (Half house)

| House Condition | Solutions/Composition | | | | Average |
|---|---|---|---|---|---|
| | 1 | 2 | 3 | 4 | |
| | | 1 & 3 | | | |
| Pre-treatment | 10 | 10 | 8800 | 1200 | 2505 |
| Day 13 | 10 | 10 | 10 | 200 | 58 |
| Day 16 | 10 | 10 | 10 | 100 | 33 |
| Day 19 | 10 | 200 | 600 | 200 | 253 |
| Day 22 | 10 | 900 | 800 | 10 | 430 |

Tables 14 and 15 present the levels of *E. coli* (Table 14) and *Clostridium* (Table 15) obtained at the litter surface down the water lines after bird placement.

TABLE 14

Field Trial - Disease Control (*E. coli.*) (cfu/swab) - Farm 5

| House Condition | Solutions/Composition | | Average |
|---|---|---|---|
| | 1 | 2 | |
| | | 3 | |
| Pre-treatment | 410 | 130 | 270 |
| Day 13 | 42000 | 34000 | 38000 |
| Day 16 | 210000 | 150000 | 180000 |
| Day 19 | 290000 | 210000 | 250000 |
| Day 22 | 340000 | 310000 | 325000 |

TABLE 15

Field Trial - Disease Control (*Clostridium*) (spores/swab) - Farm 5

| House Condition | Solutions/Composition | | Average |
|---|---|---|---|
| | 1 | 2 | |
| | | 3 | |
| Pre-treatment | 280 | 160 | 220 |
| Day 13 | 280 | 10 | 145 |
| Day 16 | 400 | 50 | 225 |
| Day 19 | 400 | 2500 | 1450 |
| Day 22 | 5400 | 1700 | 3550 |

Figure 2A:
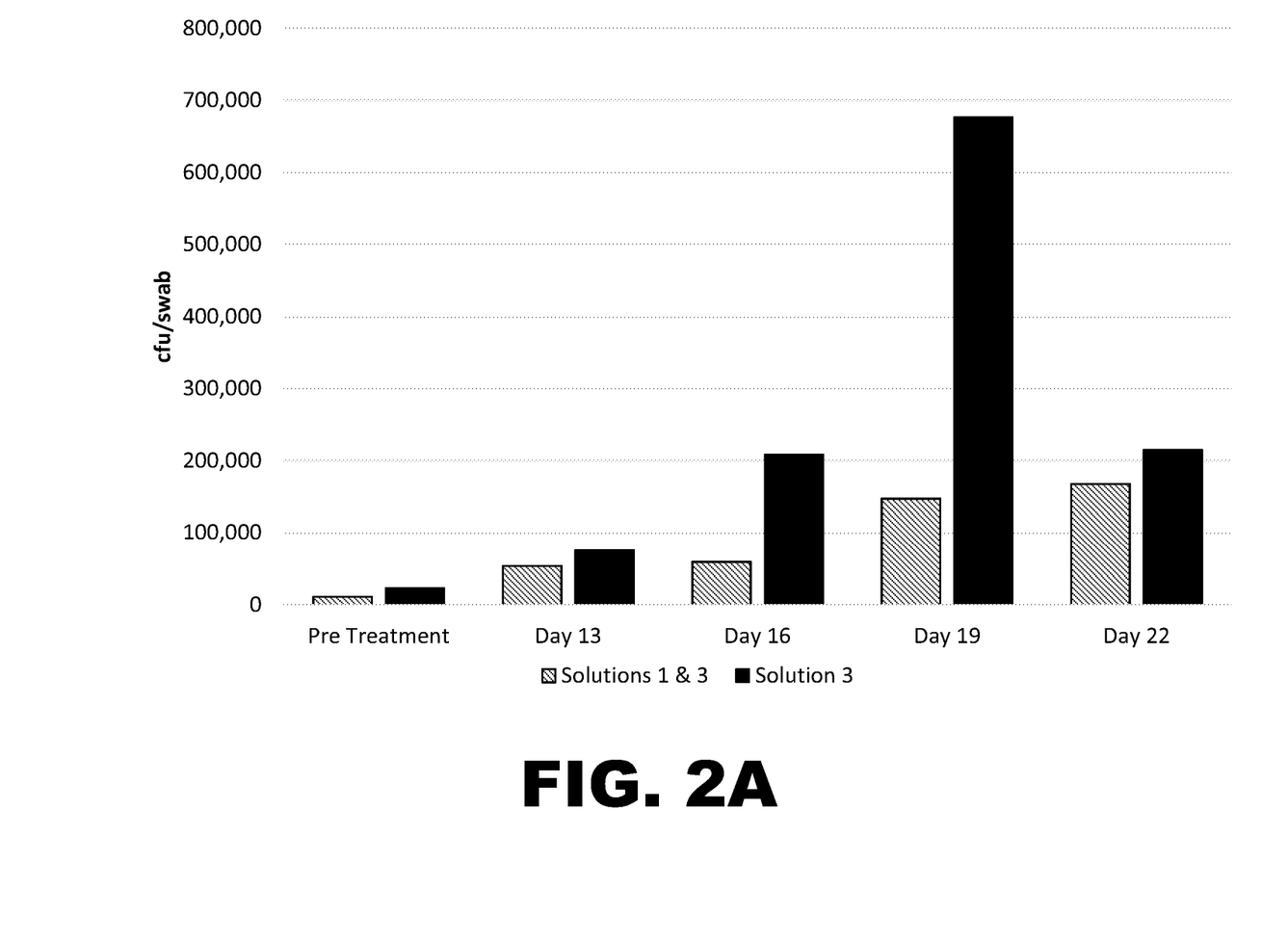
FIG. 2A and FIG. 2B depict graphs showing average of amount of *E. Coli* (FIG. 2A) and *Clostridium* (FIG. 2B) obtained from swabs collected from broiler houses treated with solution 1 and 3 or solution 3.
Figure 2B:
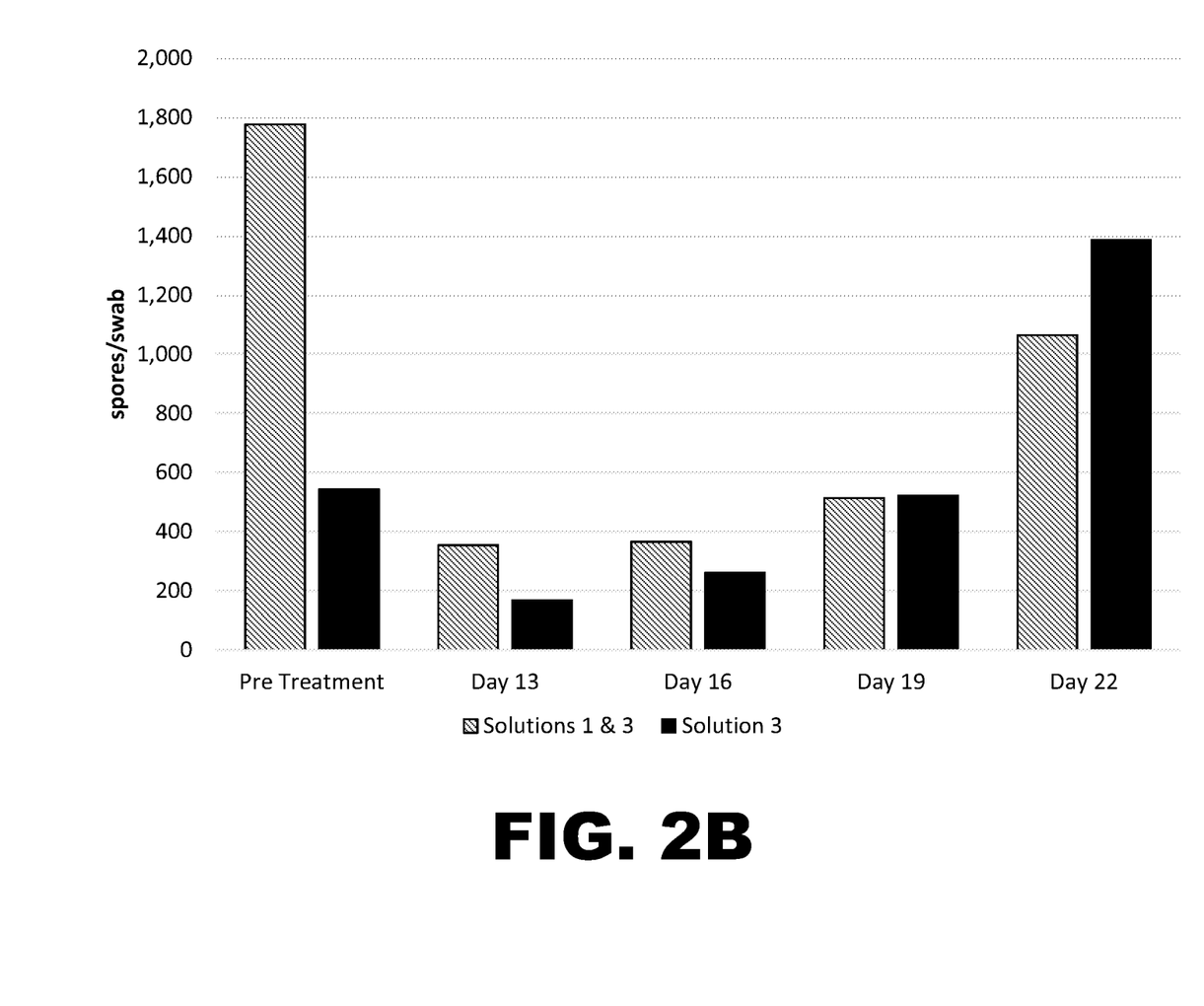

Tables 16 and 17 present the levels of *E. coli* (Table 16) and *Clostridium* (Table 17) obtained at the litter surface down the water lines after bird placement. The average number of *E. coli* colonies obtained from Farms 3-6 treated with solutions 1 and 3 and solution 3 alone is shown in FIG. 2A. The average number of *Clostridium* spores obtained from Farms 3-6 treated with solutions 1 and 3 and solution 3 alone is shown in FIG. 2B.

TABLE 16

Field Trial - Disease Control (*E. coli.*) (cfu/swab) - Farm 6

| House Condition | Solutions/Composition | | | | Average |
|---|---|---|---|---|---|
| | 1 | 2 | 3 | 4 | |
| | | | 3 | | |
| Pre-treatment | 81000 | 30000 | 19000 | 8200 | 34550 |
| Day 13 | 170000 | 150000 | 37000 | 25000 | 95500 |
| Day 16 | 190000 | 190000 | 320000 | 190000 | 222500 |
| Day 19 | 1700000 | 1300000 | 310000 | 250000 | 890000 |
| Day 22 | 80000 | 170000 | 160000 | 230000 | 160000 |

Field Trial - Disease Control (*Clostridium*) (spores/swab) - Farm 6

| House Condition | Solutions/Composition | | | | Average |
|---|---|---|---|---|---|
| | 1 | 2 | 3 | 4 | |
| | | | 3 | | |
| Pre-treatment | 1300 | 10 | 1500 | 10 | 705 |
| Day 13 | 500 | 200 | 10 | 10 | 180 |
| Day 16 | 200 | 10 | 10 | 900 | 280 |
| Day 19 | 10 | 10 | 10 | 200 | 58 |
| Day 22 | 10 | 800 | 10 | 400 | 305 |

Tables 18 and 19 present the levels of *E. coli* (Table 18) and *Clostridium* (Table 19) obtained at the floor or pad surface after bird placement.

TABLE 18

Field Trial- Disease Control (*E. coli.*) (cfu/swab) - Farm 7

| Condition | Solutions/Composition |
|---|---|
| | 3 |
| Post-treatment | 20 |
| Post-treatment (24 hours) | 10 |

TABLE 19

Field Trial - Disease Control (*Clostridium*) (TPC) - Farm 7

| Condition | Solutions/Composition |
|---|---|
| | 3 |
| Post-treatment | 164000000 |
| Post-treatment (24 hours) | 49000 |

Figure 3A:
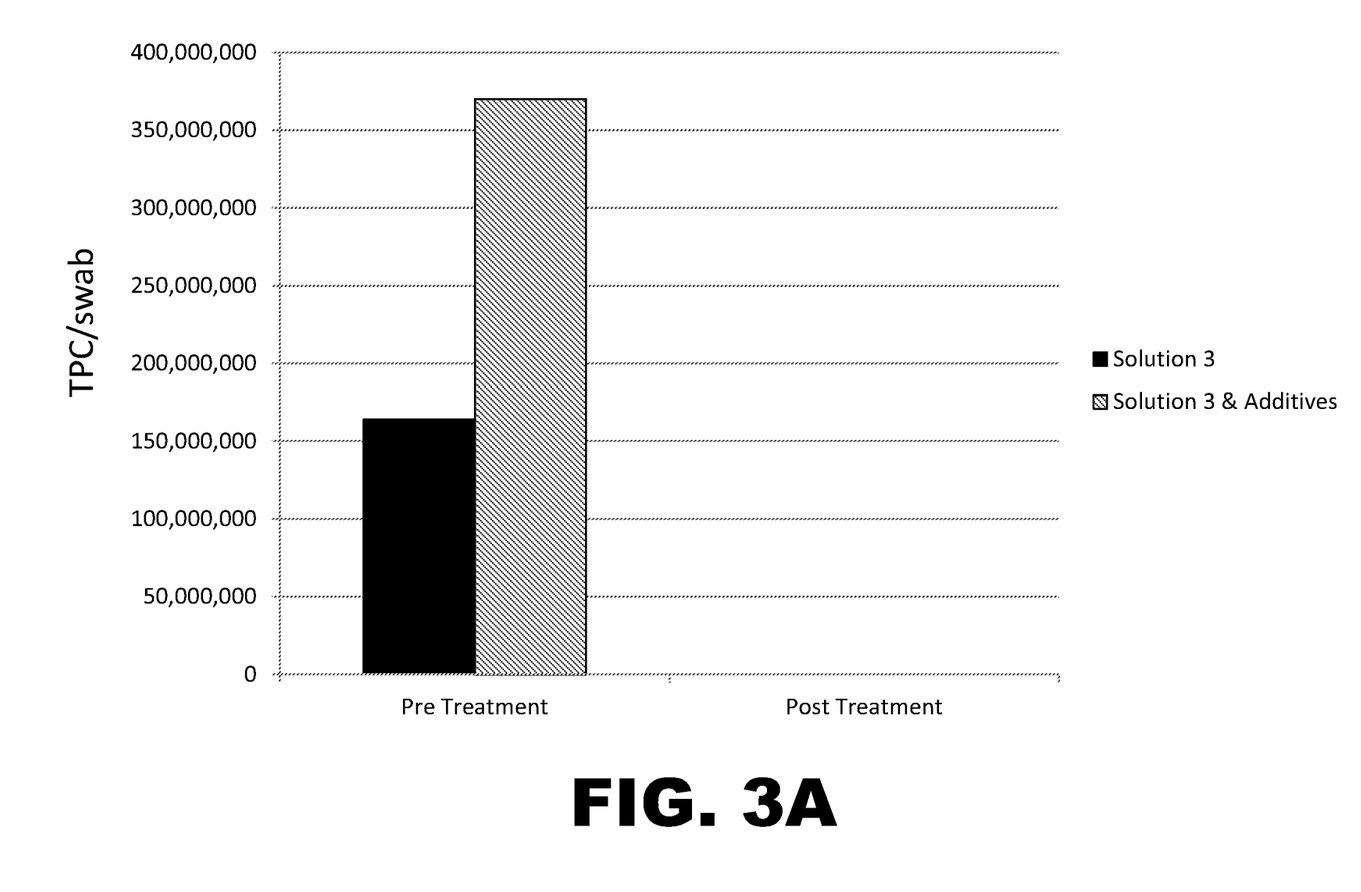
FIG. 3A and FIG. 3B depict graphs showing amount of *Clostridium* (FIG. 3A) and *E. Coli* (FIG. 3B) obtained from swabs collected from broiler houses that were treated with solution 1 and 3 or solution 3.
Figure 3B:
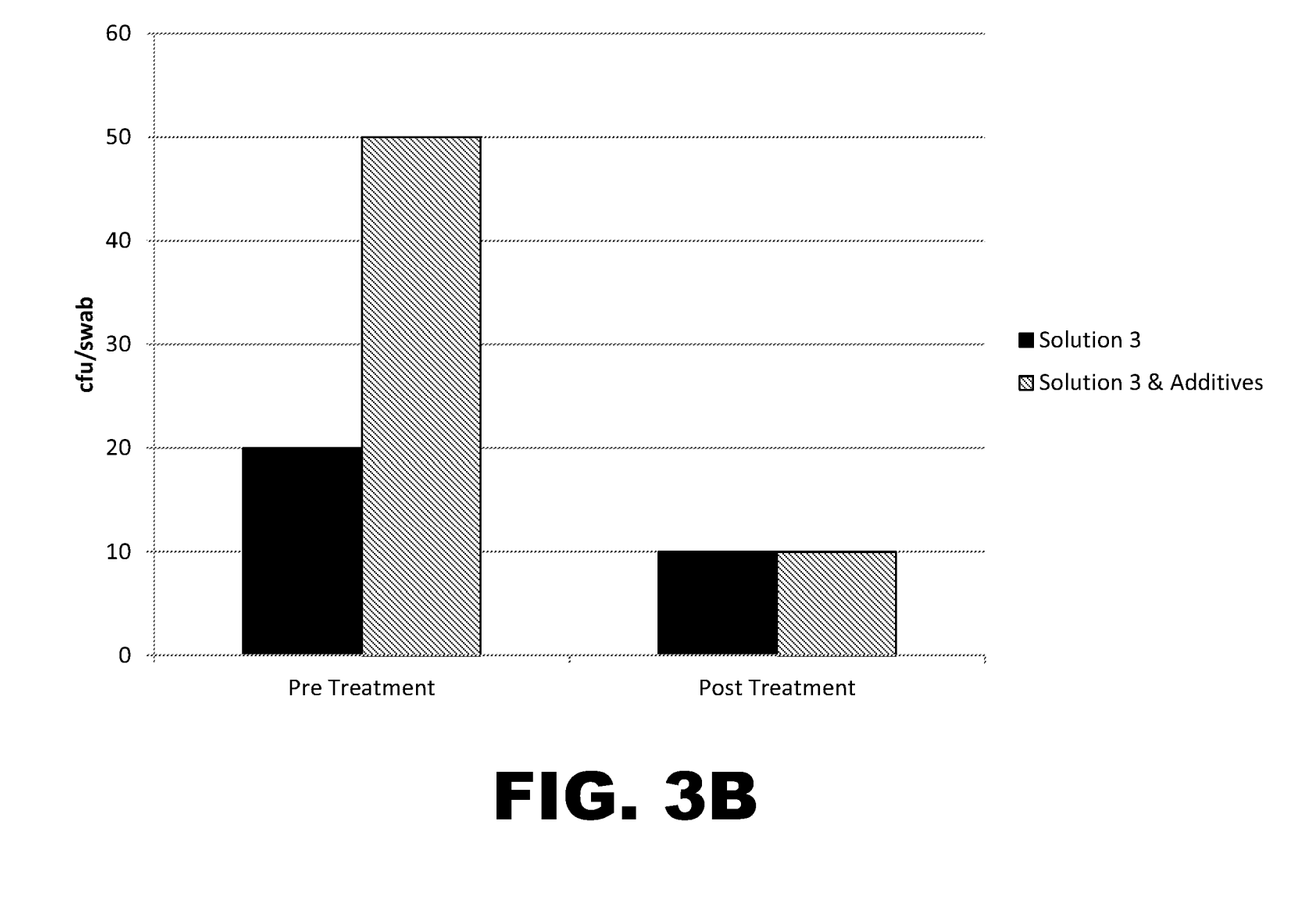

Tables 20 and 21 present the levels of *E. coli* (Table 20 and FIG. 3B) and *Clostridium* (Table 21 and FIG. 3A) obtained at the floor or pad surface between the feed and water lines after bird placement.

TABLE 20

Field Trial - Disease Control (*E. coli.*) (cfu/swab) - Farm 7

| | Composition Condition A |
|---|---|
| Post-treatment | 50 |
| Post-treatment (24 hours) | 10 |

TABLE 21

Field Trial - Disease Control (*Clostridium*) (TPC) - Farm 7

| | Composition Condition A |
|---|---|
| Post-treatment | 370000000 |
| Post-treatment (24 hours) | 10 |

What is claimed is:

1. A composition comprising about 15 wt % to about 55 wt % of a metal sulfate, about 4 wt % to about 9 wt % of an inorganic acid having a pKa of less than −1 selected from the group consisting of hydrobromic acid, hydrochloric acid, hydroiodic acid, perchloric acid, sulfuric acid, and combinations thereof, about 0.1 wt % to about 4 wt % of an organic acid selected from the group consisting of acetic acid, adipic acid, benzoic acid, butanoic acid, citric acid, formic acid, fumaric acid, glutaric acid, glycolic acid, lactic acid, mandelic acid, malic acid, propionic acid, sorbic acid, succinic acid, and combinations thereof, and about 0.001 wt % to about 0.03 wt % of iodine as an iodine complex selected from the group consisting of nonylphenoxypoly(ethyleneoxy)ethanol-iodine complex and polyoxyethylene-polyoxypropylene block polymer-iodine complex.

2. The composition of claim 1, wherein the metal sulfate is selected from the group consisting of aluminum sulfate, calcium sulfate, copper sulfate, iron(II) sulfate, magnesium sulfate, and combinations thereof.

3. The composition of claim 1, wherein the inorganic acid is selected from the group consisting of hydrochloric acid, perchloric acid, sulfuric acid, and combinations thereof.

4. The composition of claim 1, wherein the organic acid is selected from the group consisting of acetic acid, formic acid, propionic acid, and combinations thereof.

5. The composition of claim 1, wherein the metal sulfate is aluminum sulfate and is present in the amount from about 30% to about 40% by weight of the composition, the inorganic acid is sulfuric acid and is present in the amount from about 6% to about 8% by weight of the composition, the organic acid is propionic acid and is present in the amount from about 0.5% to about 3% by weight of the composition, and the iodine complex is nonylphenoxypoly(ethyleneoxy)ethanol-iodine complex and is present in the amount from about 0.005% to about 0.02% by weight of the composition.

6. The composition of claim 1, wherein the composition is a liquid.

7. A method for inhibiting microbial growth of one or more microbes in an animal facility, the method comprising contacting a surface of the animal facility with a composition comprising about 15 wt % to about 55 wt % of a metal sulfate, about 4 wt % to about 9 wt % of an inorganic acid having a pKa of less than −1 selected from the group consisting of hydrobromic acid, hydrochloric acid, hydroiodic acid, perchloric acid, sulfuric acid, and combinations thereof, about 0.1 wt % to about 4 wt % of an organic acid selected from the group consisting of acetic acid, adipic acid, benzoic acid, butanoic acid, citric acid, formic acid, fumaric acid, glutaric acid, glycolic acid, lactic acid, mandelic acid, malic acid, propionic acid, sorbic acid, succinic acid, and combinations thereof, and about 0.001 wt % to about 0.03 wt % of iodine as an iodine complex selected from the group consisting of nonylphenoxypoly(ethyleneoxy)ethanol-iodine complex and polyoxyethylene-polyoxypropylene block polymer-iodine complex.

8. The method of claim 7, wherein the metal sulfate is selected from the group consisting of aluminum sulfate, calcium sulfate, copper sulfate, iron(II) sulfate, magnesium sulfate, and combinations thereof.

9. The method of claim 7, wherein the inorganic acid is selected from the group consisting of hydrochloric acid, perchloric acid, sulfuric acid, and combinations thereof.

10. The method of claim 7, wherein the organic acid is selected from the group consisting of acetic acid, butanoic acid, formic acid, propionic acid, and combinations thereof.

11. The method of claim 7, wherein the composition is a liquid and is applied at a rate of about 15 to about 35 gallons per 1,000 sq. ft.

12. The method of claim 7, wherein the metal sulfate is aluminum sulfate and is present in an amount from about 30% to about 40% by weight of the composition, the inorganic acid is sulfuric acid and is present in an amount from about 6% to about 8% by weight of the composition, the organic acid is propionic acid and is present in an amount from about 0.5% to about 3% by weight of the composition, and the iodine complex is nonylphenoxypoly(ethyleneoxy) ethanol-iodine complex and is present in the amount from about 0.005% to about 0.02% by weight of the composition.

13. The method of claim 7, wherein the one or more microbes is selected from the group consisting of *Bacillus, Camplybacter, Clostridium, Corynebacterium, Desulfovibrionales, Escherichia, Enterococcus , Histomonas meleagridis, Lactobacillus, Listeria, Pseudomonas, Staphylococcus, Salmonella, Streptococcus*, and combinations thereof.

14. The method of claim 7, wherein the surface comprises animal litter or pads of the animal facility.

15. The method of claim 7, wherein the composition also controls ammonia levels.

16. The method of claim 15, wherein ammonia levels are reduced to at least 25 ppm as measured by a SAM IV ammonia monitor as compared to prior to contacting the surface with the composition.

\* \* \* \* \*